United States Patent [19]

D'Amico et al.

[11] Patent Number: 5,788,974
[45] Date of Patent: Aug. 4, 1998

[54] HELICOBACTER PYLORI TREATMENT COMPLIANCE PACK

[76] Inventors: Steven A. D'Amico, 3139 McClellan Dr.; Peter J. Maida, 3239 Ridgeway Dr., both of Greensburg, Pa. 15601

[21] Appl. No.: 712,070

[22] Filed: Sep. 11, 1996

[51] Int. Cl.⁶ .................................................. A01N 25/08
[52] U.S. Cl. .................... 424/405; 424/409; 424/451; 424/441; 424/464; 424/10.1; 424/10.3; 424/10.4; 514/925; 206/438; 206/534; 206/828
[58] Field of Search ............................. 424/409, 10.1, 424/10.3, 10.4, 405, 451, 456, 464, 441; 206/438, 534, 828; 514/925

[56] References Cited

U.S. PATENT DOCUMENTS

| | | | |
|---|---|---|---|
| D. 370,625 | 6/1996 | Kelsey et al. | D7/341 |
| 1,174,695 | 3/1916 | Dawson | 424/10.1 |
| 3,579,883 | 5/1971 | Hayes | 206/534 |
| 3,826,222 | 7/1974 | Romick | 116/121 |
| 4,318,477 | 3/1982 | Kerpe | 206/534 |
| 4,736,849 | 4/1988 | Leonard et al. | 206/534 |
| 5,014,851 | 5/1991 | Wick | 206/539 |
| 5,050,739 | 9/1991 | Hannan et al. | 206/531 |
| 5,256,684 | 10/1993 | Marshall | 514/398 |
| 5,323,908 | 6/1994 | Boettger | 206/532 |
| 5,489,025 | 2/1996 | Romick | 206/531 |
| 5,558,229 | 9/1996 | Halbich | 206/534 |

OTHER PUBLICATIONS

Frazer et al. NZ Med J Aug. 9, 1996, pp. 290–292, An Audit of Low Dose Therapy –Helicobacter.

P J B: Aug. 30, 1996, Dialog Fig.–129 Pmind P. & G. US Approval.

*Primary Examiner*—Neil S. Levy
*Attorney, Agent, or Firm*—James Ray & Associates

[57] ABSTRACT

A pharmaceutical dispensing container which holds multiple dosage units for aiding in the compliance in the eradication/treatment for *Helicobater pylori* and subsequent/related gastric maladies in relation to said bacterial infection using a repetative dosage regimen for a treatment period of sufficient duration to mitigate said bacterial infection formatted in such a way to gain optimal ease of compliance resulting in improved outcome of treatment. Dosage units may be antibiotic, anti microbial, or symtomatic relief agents in any combination.

6 Claims, 4 Drawing Sheets

HELICOBACTER PYLORI TREATMENT COMPLIANCE PACK

FIELD OF INVENTION

This invention relates to a container, and it subsequent methodolgy, which holds dosage units to treat *Helicobacter pylori* (*H-pylori*) induced maladies. Such infirmities include, but are not limited to; duodinal ulceration/inflammation, gastric ulceration/inflammation, erosive esophagitis and the like.

BACKGROUND OF THE INVENTION

*H-pylori*, a micro-organism which damages the protective mucosal barrier, has been found to be causative in most cases of gastric and duodenal ulceration and the like. In fact *H-pylori* has been known to exist in approximately 70% of all peptic ulcers (gastric or duodenal) and is known to be a major cause of recurrent ulceration. Recent studies show most patients to be ulcer free after *H-pylor* eradication.

SUMMARY OF THE INVENTION

This invention concerns itself with adressing some major setbacks currently being experienced with treating *H-pylori*. These include, but are not limited to:

1) Uncertainty on physicians part in prescribing the most effective/successful combinations of antibiotics/antimicrobials and/or acid suppression agents and the like.

2) Confusion/noncompliance due to, among other things, the large number of dosage units to be taken in a fairly short period of time, or forgetting whether or not a dose has been taken, or which medicines are to be taken at what time, is quite common among patients.

An objective of this invention is to overcome these common problems in a simple and inexpensive manner by providing a pharmaceutical dispensing container which presently holds, but is not limited to, 3 types of dosage units which treat *H-pylori* infection and its symptoms in specified daily regimens.

DESCRIPTION OF THE DRAWINGS

Figure 2:
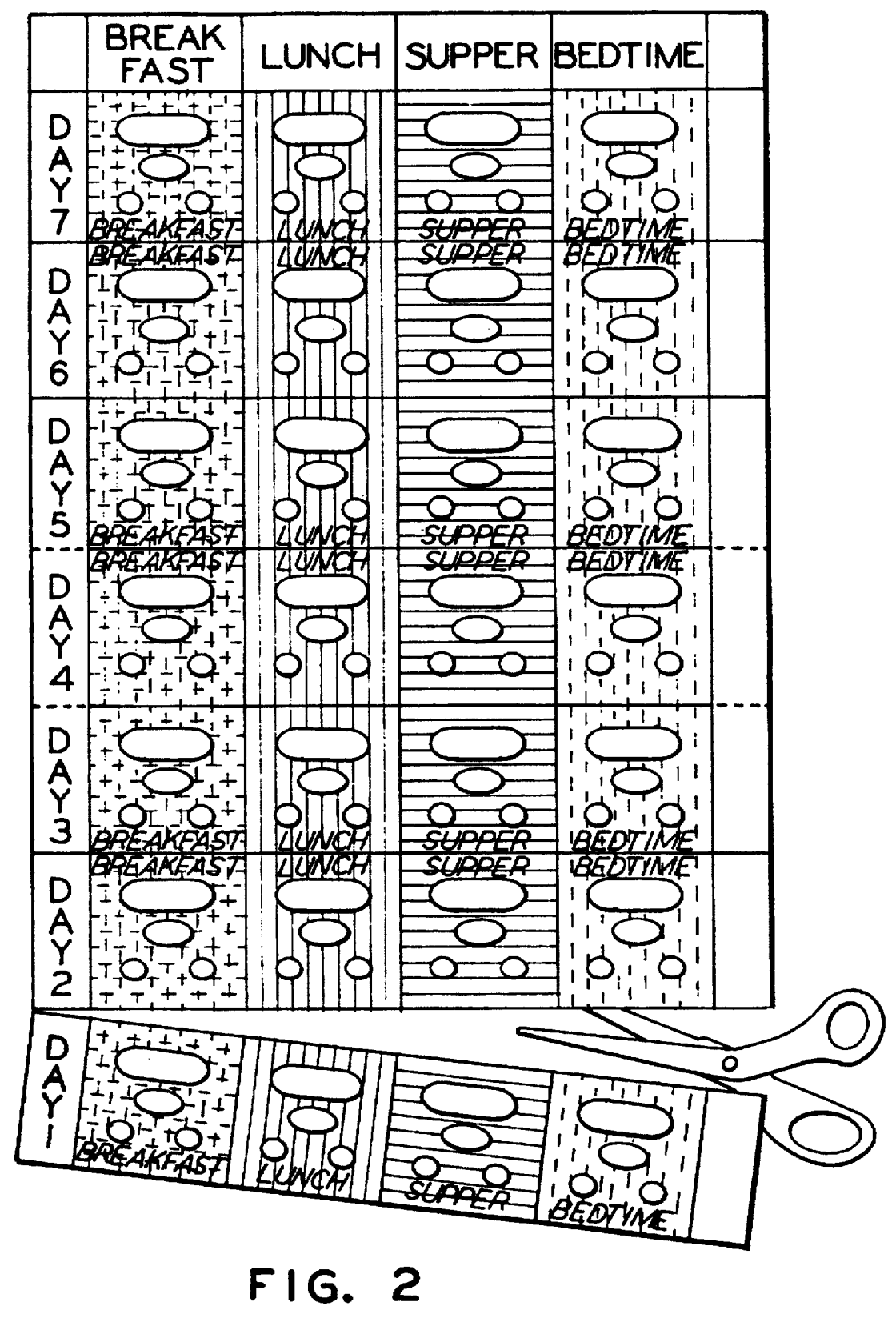

FIG. 2 is a plan view of the compliance pack of FIG. 1 depicting removal of one days' dose regimen.

PREFERRED EMBODIMENT OF THE INVENTION

Figure 1:
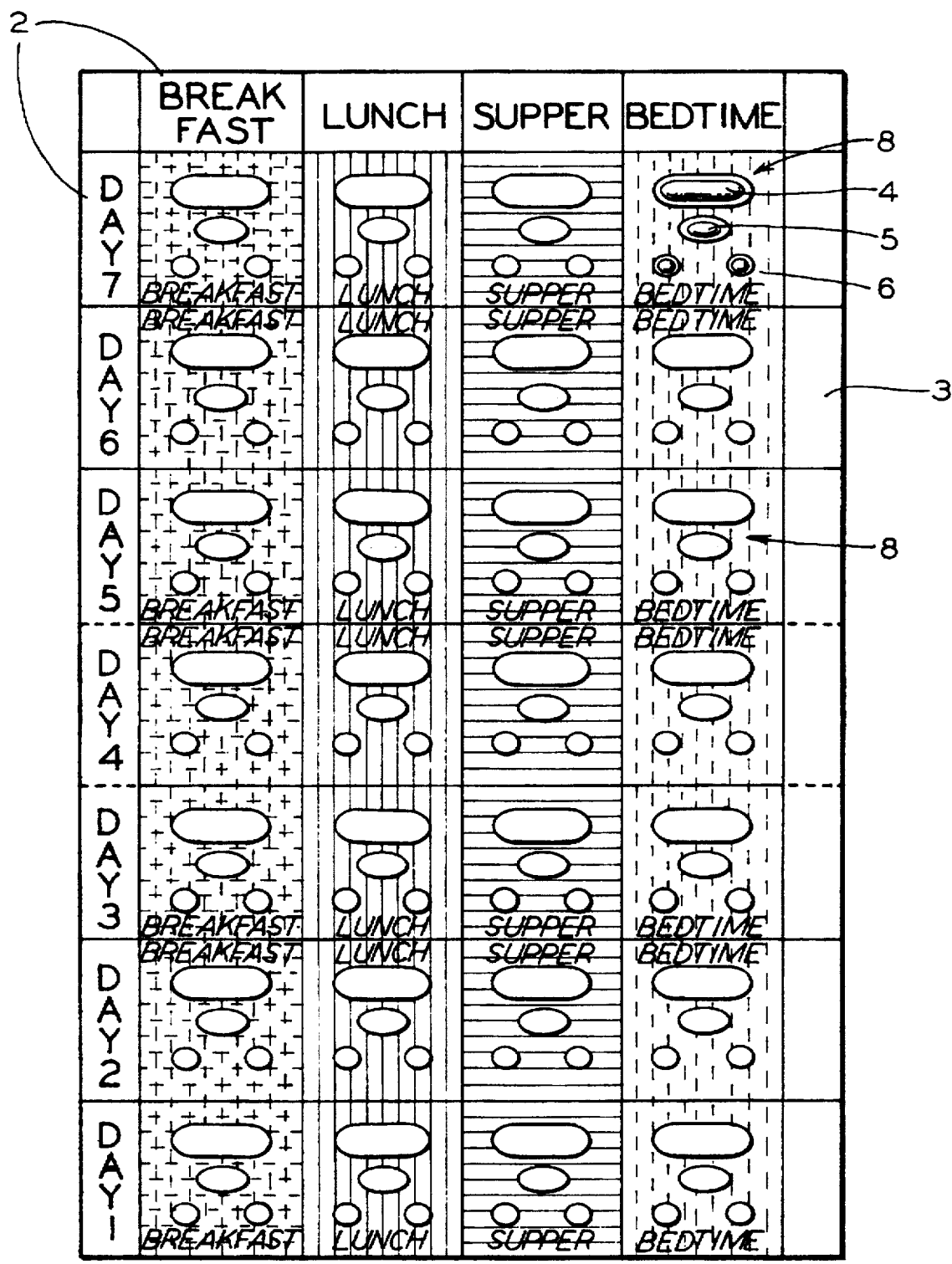
FIG. 1 is a plan view of the compliance pack of the invention showing a calendar of days and subsequent dose regimens within each of the days.

The pack specifically described in FIG. 1 is a 7 day pack divided into 4 doses of multiple agents daily. It is envisaged that the pack may be adapted for longer or shorter regimens with additional or less agents as state of the art eradication of *H-pylori* dictates, by no means is this pack limited to the dimensions or regimens described herein. By merely shortening or lengthening the pack or combining 2 packs together for two week regimens or changing the active ingredients as new, existing, or improved pharmaceutical agents are developed that offer advantages to present treatment, this pack may be adapted to meet these future demands.

A list of agents that may be used includes, but is not limited to:

ANTIBIOTICS
  Penicillin based
  Tetracyclines
  Macrolides
  Cephalosporins
  Fluoroquinolones
  Aminoglycosides etc.
or pharmaceutically acceptable salts, metabolites, and the like.

ANTIMICROBIALS
  Metronidazole
  Nitroimidazole bases
or pharmaceutically accepted salts, metabolites, and the like.

SYMPTOMATIC RELIEF PRODUCTS
  Antacids
  Bismuth containing products
  H2 receptor antagonists
  Proton pump inhibitors
or pharmaceutically acceptable salts, metabolites, and the like.

The pack shown in FIG. 1 has a representation of each agent/entity but it could be in any combination or combinations found to be safe and effective. The 4 parts per day are listed in FIG. 1 as Breakfast, Lunch Supper, and Bedtime. It is understood that taking the dosage units with meals aids in effectiveness and possibly decreases gastro-intestinal side effects.

The dose pack in FIG. 1 will contain an antibiotic, an antimicrobial, an a symptomatic relief agent. Again it is understood that it is in no way limited to these specifications, and that this example of our invention, although functional, is a representation of one embodiment of many possible forms of this invention. The pack represented in FIG. 1 is an elongated rectangular container in the form of a blister pack comprising of base (1) with a reversed day chart along the Y-axis, to aid the patient in cutting with scissors, or along a perforation so as to separate doses, one day at a time. The patient could then carry an entire days dose with them wherever they go, thus greatly facilitating and enhancing compliance, as the size of the overall box could be quite cumbersome.

Each part of the one day, detachable dose strip will be consistantly labeled by printing and color-coded to distinguish which dose is being taken and medicines/agents contained therein. The logic behind the reverse day count is that as each entire days dose is removed by the patient, the remainder of the pack will stay intact.

Along the X-axis is printing that identifies the 4 daily, divided doses, each being color coded along the entire length of the pack for consitency. It is envisaged that the breakfast column will be yellow, the lunch column will be red, the supper column will be blue, and the bedtime column will be violet.

Figure 4:
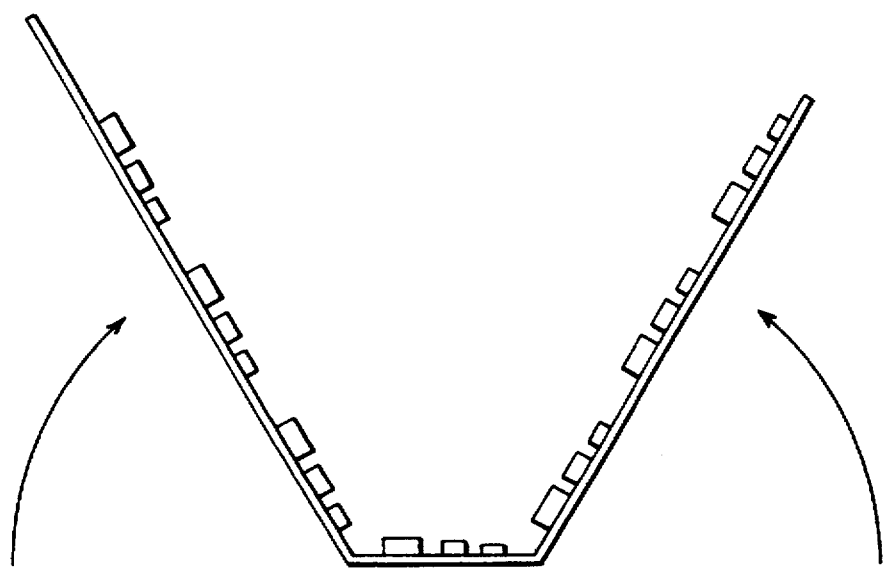
FIG. 4 is a side elevation view of the compliance pack of the invention illustrating a folding of the pack.

The actual pack will fold upon itself along both sides of "DAY 4" as shown in FIG. 1 and FIG. 4. this will aid in shipping as well as be protective of the product.

A facing strip (3) is affixed to the base (1) containing therein 3 types of discrete dosage units (4) (5) and (6) together with printed instructions (7). The facing strip, FIG. 3, generally indicated at (3) is of a conventional blister pack type in which "blisters" have been formed in a regular grid of 28 ranks and 4 files. The grid of blisters (8) is so arranged in the facing strip (3) that a file of blisters (8) is in register with each part of the daily divided doses ie. "BREAKFAST", "LUNCH" etc. on the base (1) and the 28 ranks are in register of "DAY 7", "DAY 6", etc. on the base (1).

The three types of discrete solid dosage units generally indicated at (4) (5) and (6) are in the form of capsule, tablet, tablet respectively, are all located in the close blister (8) of the facing strip (3). Dosage units contain, but are not limited to, antibiotic composition in (4), (5) contains an antimicrobial, and (6) contains symptomatic treatment.

The order of packing of the dosage units of types (4) (5) and (6) located within the blisters (8) of the facing strips (3) in register with "DAY 7", "DAY 6", etc., the different colors and shapes of the three dosage units, the color-coding of the columns, and the printed instructions along the top (X-axis), facilitates the proper compliance in taking said dosage regimens on a daily basis. In addition, by using a blister pack format, there is no doubt concerning if a certain dose has been utilized or not.

To remove any capsule (4) or tablet (5) (6) at the time indicated as shown along the top, the corresponding blister (6) that contains said units can be pressed with the finger to push the dosage units through the base (1). The base (1) and facing strips (3) of the blister packs may be constructed of any material suitable for the construction of such blister packs. For example, an aluminum foil base and a thermoplastic facing strip.

Although the administration instructions are described as being printed on the base, they may of course be written or printed on a separate surface such as a sheet of paper, a label attached to the pack, or audio/visual aids included within the pack.

The blister pack described has four parts for each day, each part consisting of 3 types of active dosage forms, are defined in the form of rank and file. Of course these parts may be represented in any geometrical configuration provided that the daily doses/days supply are clearly indicated, and said geometrical configuration does not hinder compliance and the like. As stated previously, one or more blister packs within the stated parameters may be housed in a suitable dispensing box along with printed material and/or audio/visual aids to assist in compliance with said blister pack.

The methodology of this invention is not, of course, limited to blister packs. Thus any conventional pharmaceutical container(s) are suitable. Examples thereof include, but are not limited to: bottles, vials, tubes, canisters, packets, and the like. It is realized that if, for example bottles are used, and would not have the four divided daily doses listed in chart form, the dosage units must be mutually distiguishable by some visible feature sucha as color, shape form or size, or by marking or printing therein, to indicate the separate daily dosage forms to be taken at breakfast, lunch, supper and bedtime.

Figure 3:
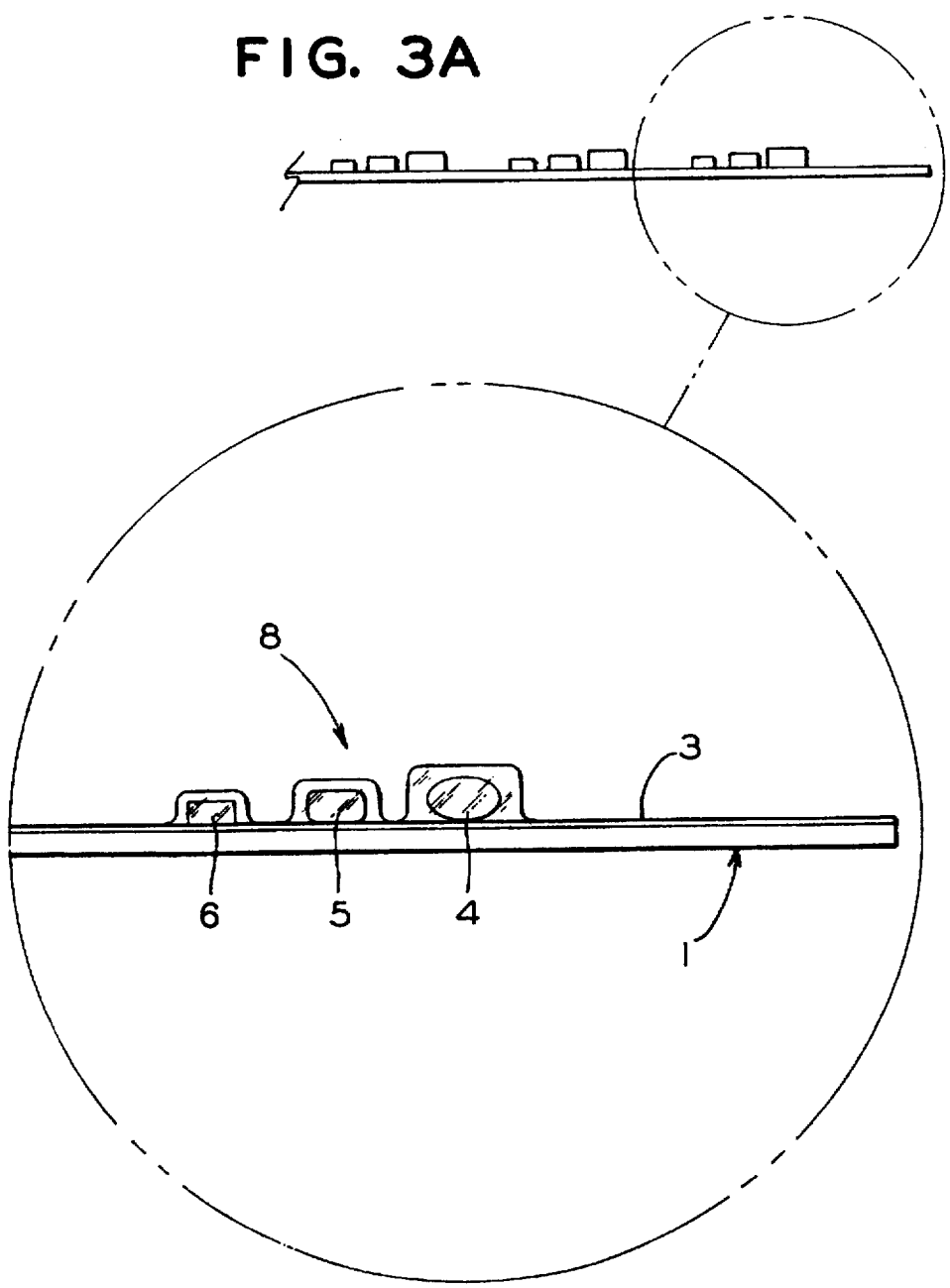
FIG. 3 is a side elevation view of the compliance pack of FIG. 1 including an exploded portion showing blisters, facings, backing and different dosage units contained within the blisters.

In the FIG. 1 and FIG. 3, capsules and tablet forms are illustrated. However any solid dosage form is suitable such as gelcaps, caplets, lozenges, gelatin capsules, chewable tablets, sprinkle, caps or effervescent dosage forms and the like. If a soft gelatin form is used it may consist of liquid, gel or solid form.

The dosage units presently are kept as separate units. As technology, stablility and pharmaceutical advancements are made, they (the dosage units) may be combined in a solid, liquid, effervescent etc. forms to simplify the regimen further. Also the capsules and tablets may contain conventional excipients well known in pharmaceutical formulation practice such as appropriate, ie; binding agents, gellants, fillers, lubricants, surfactants, flavorings or colorants.

The capsules and tablets that are being used, but are not limited to, in example FIG. 1 are:

1 capsule of tetracycline 500 mg (4)
1 tablet metronidazole 250 mg (5)
2 chewable tablets of bismuth subsalicylate 262 mg (6)

will make up one part of one day, thus every part is, but not limited to the same.

What we claim is:

1. A disposable pharmaceutically acceptable medication dispensing package containing multiple dosage units of medicants for treating *Helicobacter pylori* infection in a manner that provides a complex regimen of said medicants for consumption by a patient over the period of time necessary to eradicate the *Helicobacter pylori* bacteria in the patient, the medicants including an antibiotic chosen from the group consisting essentially of penicillin based antibiotics, tetracyclines, macrolides, cephalosporins and fluoroguinolones, and at least one symptomatic relief product chosen from the group consisting essentially of antacids, bismuth containing products, H2 receptor antagonists and proton pump inhibitor's, the package retaining and presenting said medicants at separate respective consecutive locations identified by visibly discernible indicia and the times within each day at which the medicants are to be taken by the patient, said times including each day of the week and specified times within each day presented in the form of a chart located on one face of the package wherein the days of the week are presented and the times within each day the medicants are to be taken are presented in systematic fashion, the separate respective consecutive locations of the medicants along with their identifying indicia and the identified times when the medicants are to be taken providing a consistent, regular routine that enhances compliance in prescribing and consuming the medicants over the period of time necessary to eradicate the Helicobacter pylori bacteria in the patient.

2. The package of claim 1 wherein the visibly discernible indicia include color coded blisters containing the respective medicants.

3. The package of claim 1 wherein the days of the week are listed on a first axis of the chart and package while the identified times of each day are listed on a second axis of the chart and package extending substantially perpendicular to said first axis.

4. The package of claim 1 wherein the days of the week on said chart and package are in rows that begin at the bottom of the chart and package, with each such row being removable from the bottom of the chart and package.

5. The package of claim 1 in which the medicants include an antimicrobial consisting of metronidazole or a nitroimidazole base product.

6. The package of claim 1 wherein the medicants include H2 antagonists and proton pump inhibitors.

* * * * *

UNITED STATES PATENT AND TRADEMARK OFFICE
CERTIFICATE OF CORRECTION

PATENT NO.     : 5,788,974
DATED          : August 4, 1998
INVENTOR(S)    : Steven A. D'Amico and Peter J. Maido It is certified that error appears in the above-identified patent and that said Letters Patent is hereby corrected as shown below:

Column 1,
Line 5, please delete "it", and insert -- its --;
Line 8, please delete "duodinal", and insert -- duodenal --.

Column 2,
Line 28, after "Lunch", please insert -- , --;
Line 33, please delete "an", and insert -- and --;
Line 34, please delete "it", and insert -- the dose pack --;
Line 39, please delete "of", and insert -- a --;
Line 39, after "chart", please insert -- located --;
Line 40, after "scissors", please delete -- ,or --.

Column 3,
Line 58, after "sprinkle", please delete -- , --.

Column 4,
Line 23, please delete "fluoroguinolones", and insert -- fluoroquinolones --;
Line 26, please delete "inhibitor's", and insert -- inhibitors --;
Lines 33 to 38, please delete "said times including each day of the week and specified times within each day presented in the form of a chart located on one face of the package wherein the days of the week are presented and the times within each day the medicants are to be taken are presented in systematic fashion", and insert -- said times for taking the medicants being presented on a face of the package in systematic fashion --;
Line 49, please delete "the" (both occurrences), and before "week" insert -- a --;
Line 50, please delete "chart and";
Line 52, please delete "chart and";
Line 55, please delete "chart and";
Line 56, please delete "chart and";

UNITED STATES PATENT AND TRADEMARK OFFICE
CERTIFICATE OF CORRECTION

PATENT NO.   : 5,788,974
DATED        : August 4, 1998
INVENTOR(S)  : Steven A. D'Amico and Peter J. Maido It is certified that error appears in the above-identified patent and that said Letters Patent is hereby corrected as shown below:

<u>Column 4, contd.</u>
Line 57, please delete "chart and";
Line 62, please delete "and", and insert -- or --.

Signed and Sealed this

Sixth Day of August, 2002

Attest:

Attesting Officer

JAMES E. ROGAN
Director of the United States Patent and Trademark Office